(12) United States Patent
King et al.

(10) Patent No.: US 7,977,355 B2
(45) Date of Patent: *Jul. 12, 2011

(54) N-(2-HYDROXYETHYL)-N-METHYL-4-(QUINOLIN-8-YL(1-(THIAZOL-4-YLMETHYL)PIPERIDIN-4-YLIDENE)METHYL

(75) Inventors: Megan Murphy King, Wilmington, DE (US); Cathy Dantzman, Wilmington, DE (US); Glen Ernst, Wilmington, DE (US); Thomas J. Hudzik, Wilmington, DE (US); Khanh Bui, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 17 days.

This patent is subject to a terminal disclaimer.

(21) Appl. No.: 12/643,202

(22) Filed: Dec. 21, 2009

(65) Prior Publication Data

US 2010/0160374 A1 Jun. 24, 2010

Related U.S. Application Data

(63) Continuation of application No. 11/875,014, filed on Oct. 19, 2007, now Pat. No. 7,659,286.

(60) Provisional application No. 60/862,327, filed on Oct. 20, 2006.

(51) Int. Cl.
*A61K 31/47* (2006.01)
*C07D 215/00* (2006.01)
*C07D 295/00* (2006.01)
*A61P 25/22* (2006.01)
*A61P 25/24* (2006.01)
*A61P 25/16* (2006.01)

(52) U.S. Cl. .................. 514/314; 546/176; 546/184

(58) Field of Classification Search .................. None
See application file for complete search history.

(56) References Cited

U.S. PATENT DOCUMENTS

| | | | |
|---|---|---|---|
| 2,898,339 | A | 8/1959 | Wheeler et al. |
| 4,581,171 | A | 4/1986 | Kennis et al. |
| 6,187,792 | B1 | 2/2001 | Delorme et al. |
| 6,455,545 | B2 | 9/2002 | Delorme et al. |
| 6,552,036 | B2 | 4/2003 | Boyd et al. |
| 6,693,117 | B2 | 2/2004 | Delorme et al. |
| 6,753,335 | B2 | 6/2004 | Brown et al. |
| 6,784,181 | B2 | 8/2004 | Brown et al. |
| 6,838,468 | B2 | 1/2005 | Brown et al. |
| 7,312,336 | B2 | 12/2007 | Delorme et al. |
| 7,659,286 | B2 | 2/2010 | Dantzman et al. |
| 2001/0029258 | A1 | 10/2001 | Snutch |
| 2004/0204404 | A1 | 10/2004 | Zelle et al. |
| 2006/0287361 | A1 | 12/2006 | Brown et al. |
| 2007/0066652 | A1 | 3/2007 | Brown et al. |
| 2007/0099957 | A1 | 5/2007 | Brown et al. |
| 2008/0176903 | A1 | 7/2008 | Delorme et al. |

FOREIGN PATENT DOCUMENTS

| | | |
|---|---|---|
| WO | 9828275 A1 | 7/1998 |
| WO | 9933806 A1 | 7/1999 |
| WO | 0145637 A2 | 6/2001 |
| WO | 0146166 A2 | 6/2001 |
| WO | 0174806 A1 | 10/2001 |
| WO | 02094811 A1 | 11/2002 |
| WO | 2004100952 A1 | 11/2004 |
| WO | 2004101522 | 11/2004 |
| WO | 2005087742 A1 | 9/2005 |
| WO | 2008048171 | 4/2008 |

OTHER PUBLICATIONS

Dantzman, "Strategies employed and outcomes of the multi-parameter optimization of 4-piperidin-4-ylidenemethyl-benzamides as potent and selective Delta-Opioid Receptor Agonists" Jun. 14, 2010.
Dantzman et al., "Strategies employed and outcomes of the multi-parameter optimization of 4-piperidin-4-ylidenemethyl-benzamides as potent and selective Delta-Opioid Receptor Agonists" Aug. 25, 2010, 240th ACS National Meeting, Boston, MA.
Dantzman et al., "Strategies employed and outcomes of the multiparameter optimization of 4-piperidin-4-ylidenemethyl-benzamides as potent and selective Delta-Opioid Receptor Agonists" Abstract, (Jul. 28, 2010).
Wei et al., "N,N-Diethyl-4-)phenylpiperidin-4-ylidenemethyl)benzamide: A Novel, Exceptionally Selective, Potent gamma Opioid Receptor Agonist with Oral Bioavailability and It's Analogues," J. Med. Chem., 2000, vol. 43, pp. 3895-3905.
Zhang et al., "Probes for Narcotic Receptor Mediated Phenomena. 26. 1-3 Synthesis and Biological Evaluation of Diarylmethylpiperidines as Novel, Nonpeptidic Opioid Receptor Ligands," J. Med. Chem., 1999, vol. 42, pp. 5455-5463.
Bilsky et al., "Characterization of Enantiomers of (+−)BW373U86 and Related Compounds: Highly Selective Non-Peptidic Delta Opioid Agonists," Reg. Peptides, 1994, vol. 54, pp. 25-26.
Bilsky et al., "SNC 80, A Selective, Nonpeptidic and Systemically Active Opioid Delta Agonist," J. Pharm. Exper. Ther., 1995, vol. 273, pp. 359-366.
Carson et al., "N,N-Dialkyl-4-[(8-azabicyclo[3.2.1]-oct-3-ylidene)phenylmethyl]-benzamides, potent, selective opioid agonists," Bioorganic & Medicinal Chemistry Letters, 2004, vol. 14, pp. 2109-2112.
Plobeck et al., "New Diarylmethylpiperazines as Potent and Selective Nonpeptidic Opioid Receptor Agonists with Increased In Vitro Metabolic Stability," J. Med. Chem., 2000, vol. 43, pp. 3878-3894.
Brandt et al., "Antinociceptive Effects of Delta-Opioid Agonists in Rhesus Monkeys: Effects on Chemically Induced Thermal Hypersensitivity," The Journal of Pharmacology and Experimental Therapeutics, 2001, vol. 296, No. 3, pp. 939-946.
Non-Final OA issued for U.S. Appl. No. 10/240,114 (now USP 6753335) on Sep. 25, 2003.
International Search Report issued for PCT/SE2007/000924 on Jan. 8, 2008.
Non-final OA issued for U.S. Appl. No. 11/875,014 on Mar. 19, 2009.
Notice of Allowance issued for U.S. Appl. No. 11/875,014 on Oct. 1, 2009.
Supplemental Notice of Allowability issued for U.S. Appl. No. 11/875,014 on Nov. 13, 2009.
Co-Pending U.S. Appl. No. 12/445,883, filed on Apr. 16, 2009.

*Primary Examiner* — Ardin Marschel
*Assistant Examiner* — Bong-Sook Baek
(74) *Attorney, Agent, or Firm* — Woodcock Washburn LLP

(57) ABSTRACT

N-(2-hydroxyethyl)-N-methyl-4-(quinolin-8-yl(1-(thiazol-4-ylmethyl)piperidin-4-ylidene)methyl)benzamide, pharmaceutically acceptable salts thereof, and/or mixtures thereof, as well as, pharmaceutical compositions thereof, methods of treatment therewith, and processes of making N-(2-hydroxyethyl)-N-methyl-4-(quinolin-8-yl(1-(thiazol-4-ylmethyl)piperidin-4-ylidene)methyl)benzamide and intermediates thereof.

12 Claims, No Drawings

N-(2-HYDROXYETHYL)-N-METHYL-4-(QUINOLIN-8-YL(1-(THIAZOL-4-YLMETHYL)PIPERIDIN-4-YLIDENE) METHYL

CROSS-REFERENCE TO RELATED APPLICATIONS

This application is a continuation of U.S. application Ser. No. 11/875,014, filed Oct. 19, 2007, which claims the benefit of U.S. Provisional Application No. 60/862,327, filed Oct. 20, 2006, both of which are hereby incorporated herein by reference.

The invention is directed to novel compounds, a process for preparing the compounds and intermediates related thereto, use of the compounds and pharmaceutical compositions comprised thereof The compounds are useful in therapy, and in particular for the treatment of pain, anxiety and depression.

The delta ("δ") receptor has been identified as having a role in many bodily functions such as nociceptive, motor, and cardiovascular systems, as well as in emotional regulation. Ligands for the δ receptor may therefore find potential use as analgesics, anxiolytics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia and anti-anxiety have been observed in various animal models when one or more of these receptors has been activated. Generally, selective δ receptor ligands have advantages over non-selective opioid receptor ligands for causing less side effects.

Many δ agonist compounds that have been identified in the prior art have many disadvantages in that they suffer from poor pharmacokinetics and are not anxiolytic or analgesic when administered by systemic routes.

PCT Publication WO 01/74806 describes some δ-agonists.

However, there is still a need for improved δ-agonists.

We have now surprisingly found that certain compounds exhibit one or more improved properties, i.e. improved δ agonist potency, in vivo potency, pharmacokinetics, bioavailability, in vitro stability, in vivo stability, brain penetration, and/or lower toxicity.

Described herein is N-(2-hydroxyethyl)-N-methyl-4-(quinolin-8-yl(1-(thiazol-4-ylmethyl)piperidin-4-ylidene)methyl)benzamide.

Further described herein is N-(2-hydroxyethyl)-N-methyl-4-(quinolin-8-yl(1-(thiazol-4-ylmethyl)piperidin-4-ylidene)methyl)benzamide, pharmaceutically acceptable salts thereof, prodrugs thereof, solvates thereof, and/or mixtures thereof.

Still further described herein is tert-butyl 4-((4-(N-(2-hydroxyethyl)-N-methylcarbamoyl)phenyl)(quinolin-8-yl)methylene)piperidine-1-carboxylate.

Even further described herein is N-(2-hydroxyethyl)-N-methyl-4-((piperidin-4-ylidene)(quinolin-8-yl)methyl)benzamide.

Yet even further described herein are processes of making N-(2-hydroxyethyl)-N-methyl-4-(quinolin-8-yl(1-(thiazol-4-ylmethyl)piperidin-4-ylidene)methyl)benzamide, tert-butyl 4-((4-(N-(2-hydroxyethyl)-N-methylcarbamoyl)phenyl)(quinolin-8-yl)methylene)piperidine-1-carboxylate, and N-(2-hydroxyethyl)-N-methyl-4-((piperidin-4-ylidene)(quinolin-8-yl)methyl)benzamide.

Yet even further described herein is a pharmaceutical composition comprising -(2-hydroxyethyl)-N-methyl-4-(quinolin-8-yl(1-(thiazol-4-ylmethyl)piperidin-4-ylidene)methyl) benzamide, pharmaceutically acceptable salts thereof, prodrugs thereof, solvates thereof, and/or mixtures thereof, in association with a pharmaceutically acceptable carrier.

Still yet even further described herein is a method for the therapy of pain, depression, anxiety, anxious depression, and/or Parkinsons disease in a warm-blooded animal comprising administering to said animal in need of such therapy a therapeutically effective amount of N-(2-hydroxyethyl)-N-methyl-4-(quinolin-8-yl(1-(thiazol-4-ylmethyl)piperidin-4-ylidene)methyl)benzamide, pharmaceutically acceptable salts thereof, prodrugs thereof, solvates thereof, and/or mixtures thereof.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

Embodiments identified herein as exemplary are intended to be illustrative and not limiting.

Unless otherwise indicated, any heteroatom with unsatisfied valences is assumed to have hydrogen atoms sufficient to satisfy the valences. The definitions set forth herein take precedence over definitions set forth in any patent, patent application, and/or patent application publication that may be incorporated herein by reference.

"Warm-blooded animal" includes human.

The term "protected" means the compound referred to as protected is protected with an amino-protecting group. For example, a protected N-(2-hydroxy-ethyl)-N-methyl-4-(piperidin-4-ylidene-quinolin-8-yl-methyl)-benzamide is an N-(2-hydroxy-ethyl)-N-methyl-4-(piperidin-4-ylidene-quinolin-8-yl-methyl)-benzamide that has at least one amino group protected by an amino-protecting group.

The term "amino-protecting group" refers to art-recognized moieties capable of attaching to an amino group so as to prevent the amino group from taking place in reactions occurring elsewhere on the molecule containing the amino group.

Acceptable amino-protecting groups, include but are not limited to, for example, amino-protecting groups described in "Protective Groups in Organic Synthesis", 2nd edition, John Wiley & Sons, 1991. An amino-protecting group may, for example, be a urethane type protective group (which is also referred to as a carbamate protective group), including but not limited to arylalkyloxycarbonyl groups, such as, for example, benzyloxycarbonyl; and alkoxycarbonyl groups, such as, for example, methoxycarbonyl and tert-butoxycarbonyl. Typically, the amino-protecting group is tert-butoxycarbonyl.

In one aspect, the invention provides N-(2-hydroxyethyl)-N-methyl-4-(quinolin-8-yl(1-(thiazol-4-ylmethyl)piperidin-4-ylidene)methyl)benzamide, pharmaceutically acceptable salts thereof, prodrugs thereof, solvates thereof, and mixtures thereof.

In one embodiment, the compound of the present invention may be selected from N-(2-hydroxyethyl)-N-methyl-4-(quinolin-8-yl(1-(thiazol-4-ylmethyl)piperidin-4-ylidene) methyl)benzamide, pharmaceutically acceptable salts thereof, solvates thereof, and mixtures thereof.

In another embodiment, the compound of the present invention may be selected from N-(2-hydroxyethyl)-N-methyl-4-(quinolin-8-yl(1-(thiazol-4-ylmethyl)piperidin-4-ylidene)methyl)benzamide, pharmaceutically acceptable salts thereof, and mixtures thereof.

In a further embodiment, the compound of the present invention may be selected from N-(2-hydroxyethyl)-N-methyl-4-(quinolin-8-yl(1-(thiazol-4-ylmethyl)piperidin-4-ylidene)methyl)benzamide.

It will also be understood that certain compounds of the present invention may exist in solvated, for example hydrated, as well as unsolvated forms. It will further be understood that the present invention encompasses all such solvated forms of the compound.

Within the scope of the invention are also salts of the compound. Generally, pharmaceutically acceptable salts of a compound of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The compounds of the present invention are useful in therapy, especially for the treatment of various pain conditions, such as, for example, chronic pain, neuropathic pain, acute pain, cancer pain, pain caused by rheumatoid arthritis, migraine, visceral pain etc. This list should however not be interpreted as exhaustive.

The compounds of the present invention are useful in treating anxiety, such as, for example, panic disorder, panic disorder without agoraphobia, panic disorder with agoraphobia, agoraphobia without history of panic disorder, specific phobia, social phobia, social anxiety disorder, obsessive-compulsive disorder, stress related disorders, posttraumatic stress disorder, acute stress disorder, generalized anxiety disorder, or generalized anxiety disorder due to a general medical condition.

At least one embodiment of the present invention is useful to treat depression, such as, for example, anxious depression, major depressive disorder, dysthymic disorder, bipolar depression and/or bipolar mania, bipolar I with or without manic, depressive or mixed episodes, bipolar II, cyclothymiac disorder, mood disorder due to a general medical condition, manic episodes associated with bipolar disorder, and mixed episodes associated with bipolar disorder.

Compounds of the invention are useful for the treatment of diarrhoea, depression, anxiety and/or stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Within the scope of the invention is the use of any compound defined above for the manufacture of a medicament.

Also within the scope of the invention is the use of any compound of the invention for the manufacture of a medicament for the therapy of pain including, but not limited to: acute pain, chronic pain, neuropathic pain, back pain, cancer pain, and visceral pain.

Also within the scope of the invention is the use of any compound of the invention for the manufacture of a medicament for the therapy of anxiety, including, but not limited to: panic disorder, panic disorder without agoraphobia, panic disorder with agoraphobia, agoraphobia without history of panic disorder, specific phobia, social phobia, social anxiety disorder, obsessive-compulsive disorder, posttraumatic stress disorder, acute stress disorder, generalized anxiety disorder, or generalized anxiety disorder due to a general medical condition.

Also within the scope of the invention is the use of any compound of the invention for the manufacture of a medicament for the therapy of depression, such as, for example, major depressive disorder, dysthymic disorder, bipolar depression and/or bipolar mania, bipolar I with or without manic, depressive or mixed episodes, bipolar II, cyclothymic disorder, mood disorder due to a general medical condition, manic episodes associated with bipolar disorder, or mixed episodes associated with bipolar disorder.

Also within the scope of the invention is the use of any compound of the invention for the manufacture of a medicament for the therapy of anxious depression.

Also within the scope of the invention is the use of any compound of the invention for the manufacture of a medicament for the therapy of Parkinson's disease.

Also within the scope of the invention is the use of any of the compounds of the present invention, for the manufacture of a medicament for the treatment of any of the conditions discussed above.

A further aspect of the invention is a method for the treatment of a subject suffering from any of the conditions discussed above, whereby an effective amount of a compound of the present invention, is administered to a patient in need of such treatment.

Thus, the invention provides a compound, or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition.

This definition also encompasses prophylactic therapies for prevention of recurring conditions and continued therapy for chronic disorders.

In yet another embodiment a compound in accordance with the present invention, or a pharmaceutical composition or formulation comprising at least one compound of the present invention may be administered concurrently, simultaneously, sequentially or separately with at least one other pharmaceutically active compound selected from the following:

(i) antidepressants, including but not limited to, for example, agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine, and equivalents and pharmaceutically active isomer(s) and metabolite(s) thereof;

(ii) atypical antipsychotics, including, but not limited to, for example, quetiapine and pharmaceutically active isomer(s) and metabolite(s) thereof;

(iii) antipsychotics, including, but not limited to, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and metabolite(s) thereof;

(iv) anxiolytics including, but not limited to, for example, alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam, and equivalents and pharmaceutically active isomer(s) and metabolite(s) thereof;

(v) anticonvulsants, including, but not limited to, for example, carbamazepine, valproate, lamotrogine, gabapentin, and equivalents and pharmaceutically active isomer(s) and metabolite(s) thereof;

(vi) Alzheimer's therapies, including, but not limited to, for example, donepezil, memantine, tacrine, and equivalents and pharmaceutically active isomer(s) and metabolite(s) thereof;

(vii) Parkinson's therapies, including, but not limited to, for example, deprenyl, L-dopa, Requip, Mirapex, MAOB inhibitors (i.e. selegine and rasagiline), comP inhibitors (i.e. Tasmar), A-2 inhibitors, dopamine reuptake inhibitors, NMDA antagonists, Nicotine agonists, Dopamine agonists, and inhibitors of neuronal nitric oxide synthase, and equivalents and pharmaceutically active isomer(s) and metabolite(s) thereof;

(viii) migraine therapies, including, but not limited to, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies, including, but not limited to, for example, abciximab, activase, NXY-059, citicoline, crobenetine, desmoteplase, repinotan, traxoprodil, and equivalents and pharmaceutically active isomer(s) and metabolite(s) thereof;

(x) urinary incontinence therapies, including, but not limited to, for example, darafenacin, falvoxate, oxybutynin, propiverine, robalzotan, solifenacin, tolterodine, and equivalents and pharmaceutically active isomer(s) and metabolite(s) thereof;

(xi) neuropathic pain therapies, including, but not limited to, for example, gabapentin, lidoderm, pregablin, and equivalents and pharmaceutically active isomer(s) and metabolite(s) thereof;

(xii) nociceptive pain therapies, including, but not limited to, for example, celecoxib, etoricoxib, lumiracoxib, rofecoxib, valdecoxib, diclofenac, loxoprofen, naproxen, paracetamol, and equivalents and pharmaceutically active isomer(s) and metabolite(s) thereof;

(xiii) insomnia therapies, including, but not limited to, for example, agomelatine, allobarbital, alonimid, amobarbital, benzoctamine, butabarbital, capuride, chloral, cloperidone, clorethate, dexclamol, eszopiclone, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem, and equivalents and pharmaceutically active isomer(s) and metabolite(s) thereof; and (xiv) mood stabilizers, including, but not limited to, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this invention within the dosage range described herein and the other pharmaceutically active compound or compounds within approved dosage ranges and/or the dosage described in a relevant publication.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

A "therapeutically effective amount" and/or dosage range for compounds of the present invention may be determined by one of ordinary skill in the art via known criteria including age, weight, and response of the individual patient, and interpreted within the context of the disease being treated and/or prevented. Exemplary single or divided dosage amounts for a mammal may be from about 0.05 to about 300 mg/kg/day.

The specific dose level and frequency of dosage for any particular subject, however, may vary and generally depends on a variety of factors, including, but not limited to, for example, the bioavailability of the compounds of the present invention in the administered form; metabolic stability and length of action of the specific compounds of the present invention; species, age, body weight, general health, sex, and diet of the subject; mode and time of administration; rate of excretion; drug combination; and severity of the particular condition.; and any other factors normally considered by an attending physician when determining the individual regimen and dosage level that is the most appropriate for a particular patient.

Additionally, there is provided a pharmaceutical composition comprising a compound of the present invention, solvates thereof, or a pharmaceutically acceptable salt thereof, in association with a pharmaceutically acceptable carrier.

Particularly, there is provided a pharmaceutical composition comprising a compound of the present invention, solvates thereof, or a pharmaceutically acceptable salt thereof, in association with a pharmaceutically acceptable carrier for therapy, more particularly for therapy of pain and anxiety.

Further, there is provided a pharmaceutical composition comprising a compound of the present invention, solvates thereof, or a pharmaceutically acceptable salt thereof, in association with a pharmaceutically acceptable carrier use in any of the conditions discussed above.

Even further, there is provided a pharmaceutical composition comprising a compound of the present invention, solvates thereof, or a pharmaceutically acceptable salt thereof, in association with a pharmaceutically acceptable carrier for the therapy of depression.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (per cent by weight), more preferably from 0.10 to 50% w, of the compound of the invention, all percentages by weight being based on total composition.

In a further aspect, the present invention provides a method of preparing the compounds of the present invention.

In one embodiment, the invention provides a process for preparing N-(2-hydroxyethyl)-N-methyl-4-(quinolin-8-yl(1-(thiazol-4-ylmethyl)piperidin-4-ylidene)methyl)benzamide, comprising reacting N-(2-hydroxy-ethyl)-N-methyl-4-(piperidin-4-ylidene-quinolin-8-yl-methyl)-benzamide with 4-thiazolecarboxaldehyde in the presence of a reducing agent such as sodium triacetoxyborohydride, or sodium borohydride.

In another embodiment, the invention provides a process for preparing N-(2-hydroxy-ethyl)-N-methyl-4-(piperidin-4-ylidene-quinolin-8-yl-methyl)-benzamide comprising reacting a protected 4-(bromo-{4-[(2-hydroxy-ethyl)-methyl-carbamoyl]-phenyl}-methylene)-piperidine with 8-quinolineboronic acid to form a protected N-(2-hydroxy-ethyl)-N-methyl-4-(piperidin-4-ylidene-quinolin-8-yl-methyl)-benzamide and deprotecting said protected N-(2-hydroxy-ethyl)-N-methyl-4-(piperidin-4-ylidene-quinolin-8-yl-methyl)-benzamide.

In a particular embodiment, said protected 4-(bromo-{4-[(2-hydroxy-ethyl)-methyl-carbamoyl]-phenyl}-methylene)-piperidine is protected with a tert-Boc group at 1-piperidine position.

In a particular embodiment, said protected N-(2-hydroxy-ethyl)-N-methyl-4-(piperidin-4-ylidene-quinolin-8-yl-methyl)-benzamide is protected with a tert-Boc group at 1-piperidine position.

In a further embodiment, the invention provides a process for preparing a protected 4-(bromo-{4-[(2-hydroxy-ethyl)-methyl-carbamoyl]-phenyl}-methylene)-piperidine comprising reacting 2-(methylamino)ethanol with a protected 4-[bromo-(4-carboxy-phenyl)-methylene]-piperidine.

In a particular embodiment, said protected 4-(bromo-{4-[(2-hydroxy-ethyl)-methyl-carbamoyl]-phenyl}-methylene)-piperidine is protected with a tert-Boc group at 1-piperidine position.

In a particular embodiment, said protected 4-[bromo-(4-carboxy-phenyl)-methylene]-piperidine is protected with a tert-Boc group at 1-piperidine position.

Another embodiment is directed to a process for preparing a protected N-(2-hydroxy-ethyl)-N-methyl-4-(piperidin-4-ylidene-quinolin-8-yl-methyl)-benzamide comprising reacting a protected 4-(bromo-{4-[(2-hydroxy-ethyl)-methyl-carbamoyl]-phenyl}-methylene)-piperidine with 8-quinolineboronic acid.

Yet another embodiment, is directed to a process of deprotecting the protected N-(2-hydroxy-ethyl)-N-methyl-4-(piperidin-4-ylidene-quinolin-8-yl-methyl)-benzamide to form N-(2-hydroxy-ethyl)-N-methyl-4-(piperidin-4-ylidene-quinolin-8-yl-methyl)-benzamide.

An even further embodiment is directed to reacting the N-(2-hydroxy-ethyl)-N-methyl-4-(piperidin-4-ylidene-quinolin-8-yl-methyl)-benzamide with thiazole-4-carbaldehyde to form N-(2-hydroxyethyl)-N-methyl-4-(quinolin-8-yl(1-(thiazol-4-ylmethyl)piperidin-4-ylidene)methyl) benzamide.

In one embodiment, said protected N-(2-hydroxy-ethyl)-N-methyl-4-(piperidin-4-ylidene-quinolin-8-yl-methyl)-benzamide is protected with a tert-Boc group at the 1-piperidine position.

In another embodiment, said protected 4-(bromo-{4-[(2-hydroxy-ethyl)-methyl-carbamoyl]-phenyl}-methylene)-piperidine is protected with a tert-Boc group at the 1-piperidine position.

A still further embodiment is directed to a process for preparing N-(2-hydroxyethyl)-N-methyl-4-(quinolin-8-yl(1-(thiazol-4-ylmethyl)piperidin-4-ylidene)methyl)benzamide comprising reacting 2-(methylamino)ethanol with 4-((1-(tert-butoxycarbonyl)piperidin-4-ylidene)bromomethyl) benzoic acid to form tert-butyl 4-((4-(N-(2-hydroxyethyl)-N-methylcarbamoyl)phenyl)bromomethylene)piperidine-1- carboxylate; reacting the tert-butyl 4-((4-(N-(2-hydroxyethyl)-N-methylcarbamoyl)phenyl)bromomethylene)piperidine-1-carboxylate with 8-quinolineboronic acid to form tert-butyl 4-((4-(N-(2-hydroxyethyl)-N-methylcarbamoyl)phenyl)(quinolin-8-yl)methylene)piperidine-1-carboxylate; deprotecting the tert-butyl 4-((4-(N-(2-hydroxyethyl)-N-methylcarbamoyl)phenyl)(quinolin-8-yl)methylene)piperidine-1-carboxylate to form N-(2-hydroxyethyl)-N-methyl-4-((piperidin-4-ylidene)(quinolin-8-yl)methyl)benzamide; and reacting the N-(2-hydroxyethyl)-N-methyl-4-((piperidin-4-ylidene)(quinolin-8-yl)methyl)benzamide with thiazole-4-carbaldehyde to form the N-(2-hydroxyethyl)-N-methyl-4-(quinolin-8-yl(1-(thiazol-4-ylmethyl)piperidin-4-ylidene)methyl)benzamide.

Another embodiment is directed to tert-butyl 4-((4-(N-(2-hydroxyethyl)-N-methylcarbamoyl)phenyl)(quinolin-8-yl)methylene)piperidine-1-carboxylate.

Yet another embodiment is directed to N-(2-hydroxyethyl)-N-methyl-4-((piperidin-4-ylidene)(quinolin-8-yl)methyl)benzamide.

In general, the compound of the invention can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art. Combinatorial techniques can be employed in the preparation of compounds, for example, where the intermediates possess groups suitable for these techniques.

Scheme 1

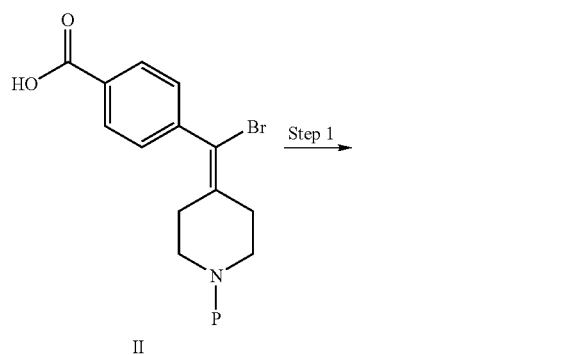

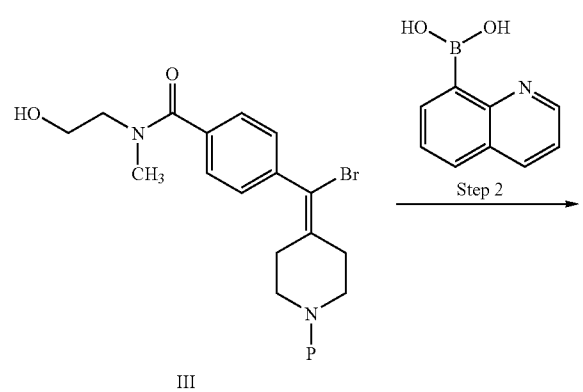

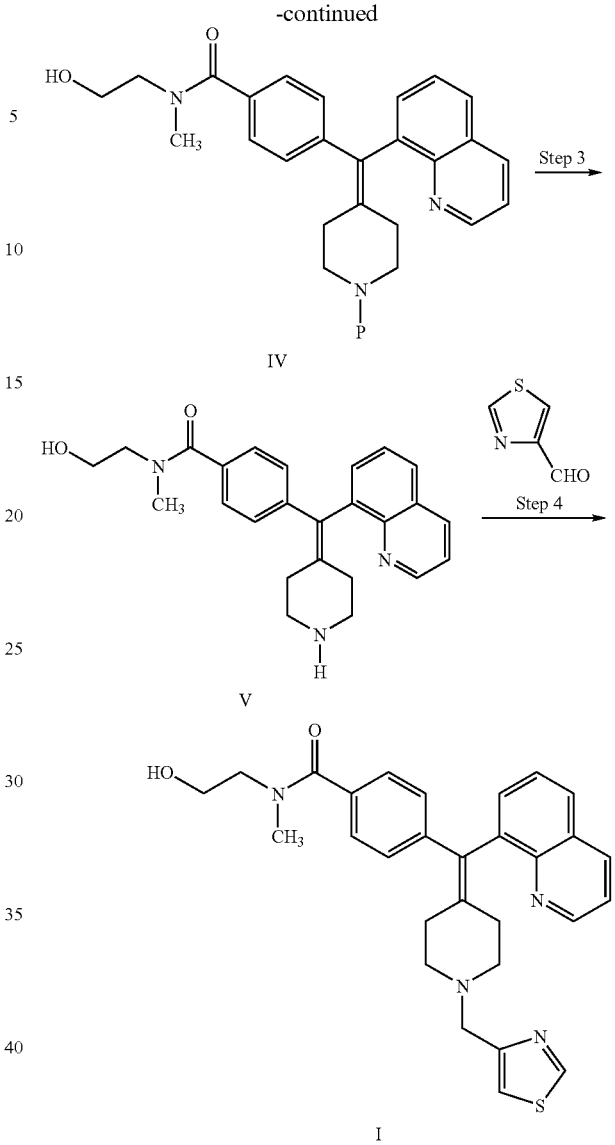

wherein P is an amino-protecting group.

Step 1

Compounds in accordance with formula III can be obtained by reacting a compound in accordance with formula II, which can be prepared in accordance with the process set forth for compound 5 in WO 2001/074806, with 2-(methylamino)ethanol in the presence of a catalyst, such as, for example, N-methylmorpholine and dimethylaminopyridine; a solvent, such as, for example, DMF and acetonitrile; and an appropriate coupling reagent, such as, for example, O-(benzotriazol-1-yl)-N,N,N',N'-tetramethyluronium tetrafluoroborate, N-(3-dimethylaminopropyl)-N'-ethylcarbodiimide hydrochloride, and carbonyl diimidazole.

Step 2

Compounds in accordance with formula IV can be obtained by coupling a compound in accordance with formula III with 8-quinolineboronic acid in the presence of a catalyst, such as, for example, dihydrogen dichlorobis(di-tert-butyl phosphinito-kP) palladate(2-), palladium(II)acetate, PdCl$_2$dppf, and PdCl$_2$(PPh$_3$)$_2$; a base, such as for example, potassium carbonate, cesium carbonate, sodium hydroxide, and potassium hydroxide; a solvent, such as, for example, isopropyl alcohol and acetonitrile/water at elevated temperatures; and optionally followed by purification with Si-Thiol, which is commercially available from SiliCycle, Inc, Quebec, Canada in a solvent, such as, for example, tetrahydrofuran. Compounds in accordance with formula IV may be optionally further crystallized out of solvent.

Step 3

Compounds in accordance with formula V can be obtained by treating compounds in accordance with formula IV with an acid, such as, for example hydrochloric acid in the presence of a solvent, such as, for example, dioxane, dichloromethane, methanol/dichloromethane, and ether/dioxane optionally followed by treatment with a base, such as, for example, sodium methoxide in a solvent, such as, for example, methanol.

Step 4

Compounds in accordance with formula I can be obtained by reacting a compound in accordance with formula V with 4-thiazolecarboxaldehyde in the presence of an appropriate borohydride reagent, such as, for example, sodium triacetoxyborohydride in a solvent, such as, for example, dichloroethane, tetrahydrofuran/methanol, and dichloroethane/methanol.

More particularly, the compound of the present invention and intermediates used for the preparation thereof can be prepared according to the synthetic routes as exemplified in the following scheme 2.

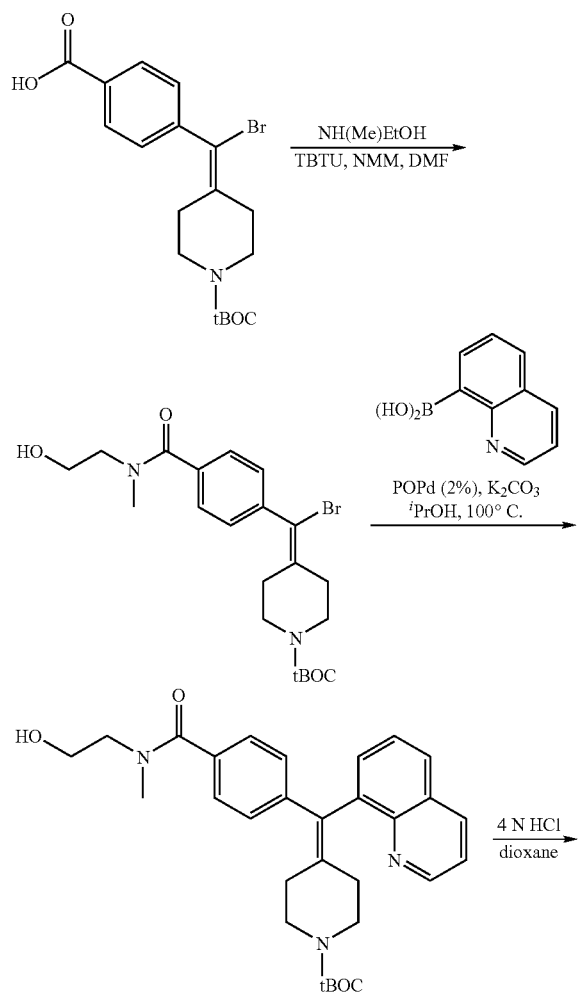

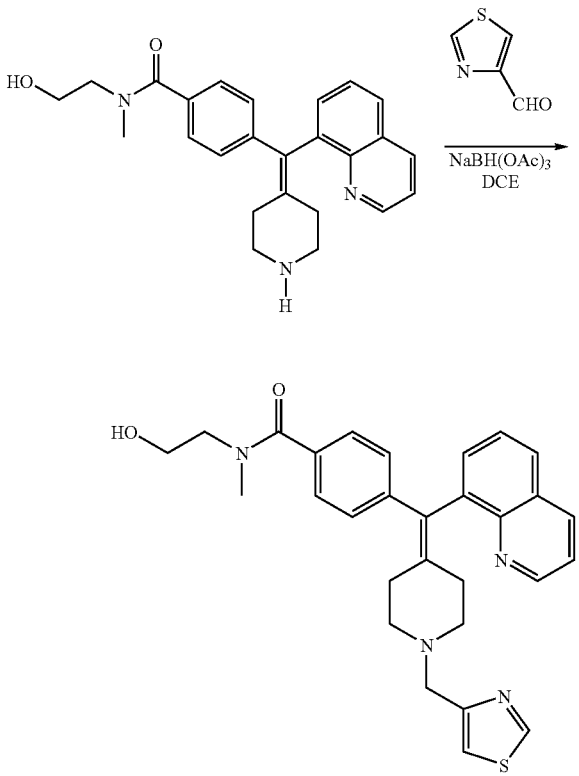

Abbreviations:

| | |
|---|---|
| TBTU = | O-(benzotriazol-1-yl)-N,N,N'N'-tetramethyluronium tetrafluoroborate |
| POPd = | dihydrogen dichlorobis(di-tert-butyl phosphinito-kP) palladate(2-) |
| NMM = | N-methylmorpholine |
| DCE = | dichloroethane |

Even more particularly, the compound of the present invention and intermediates used for the preparation thereof can be prepared according to the synthetic routes as exemplified in the following scheme 3.

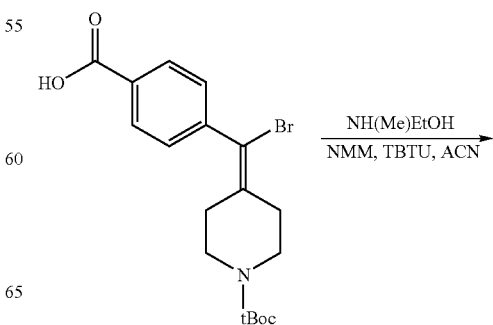

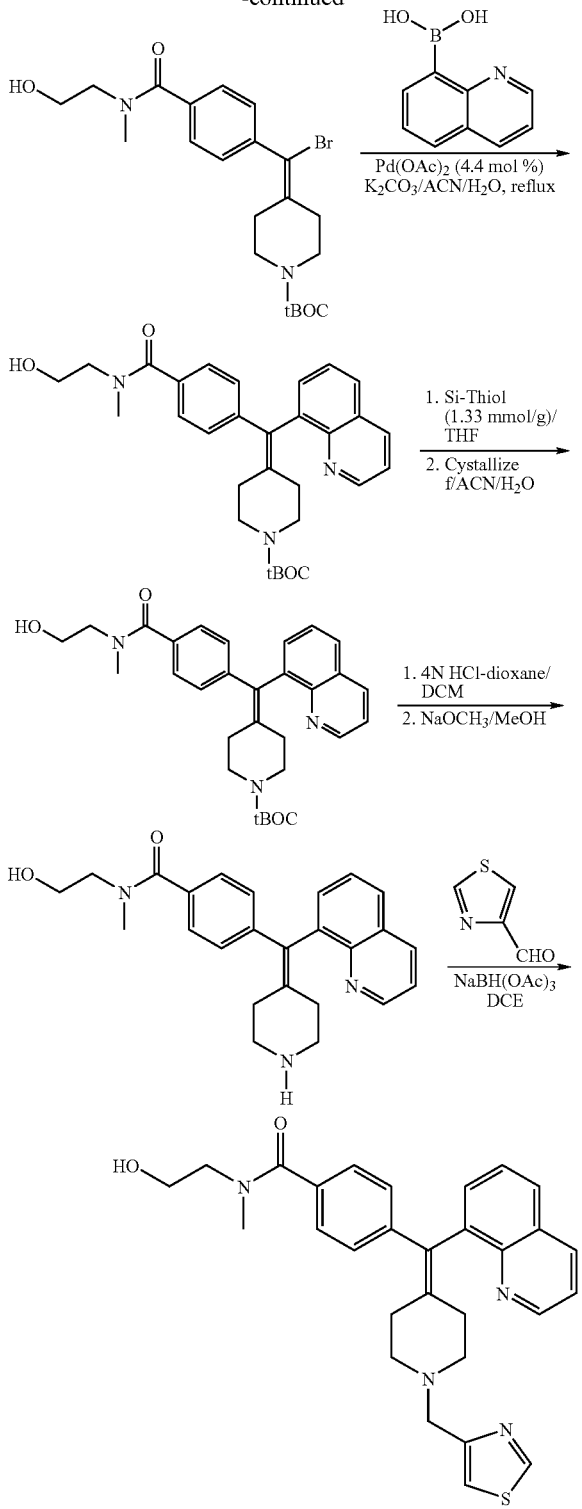

Abbreviations:

| | |
|---|---|
| TBTU = | O-(benzotriazol-1-yl)-N,N,N'N'-tetramethyluronium tetrafluoroborate |
| NMM = | N-methylmorpholine |
| ACN = | acetonitrile |
| Pd(OAc)$_2$ = | Palladium (II) acetate |
| K$_2$CO$_3$ = | Potassium carbonate |
| THF = | tetrahydrofuran |
| DCM = | dichloromethane |
| NaOCH$_3$ = | sodium methoxide |
| MeOH = | Methanol |
| NaBH(OAc)$_3$ = | Sodium triacetoxyborohydride |
| DCE = | Dichloroethane |

Biological Evaluation and Properties

The compounds of the invention are found to be active towards δ receptors in warm-blooded animal, e.g., human. Particularly the compounds of the invention are found to be effective δ receptor ligands. In vitro assays, infra, demonstrate these surprising activities, especially with regard to agonists potency and efficacy as demonstrated in the human δ receptor functional assay. This feature may be related to in vivo activity and may not be linearly correlated with binding affinity. In these in vitro assays, a compound is tested for their activity toward δ receptors and IC$_{50}$ is obtained to determine the selective activity for a particular compound towards δ receptors. In the current context, IC$_{50}$ generally refers to the concentration of the compound at which 50% displacement of a standard radioactive δ receptor ligand has been observed.

The activities of the compound towards κ and μ receptors are also measured in a similar assay.

In Vitro Models
Cell Culture

Human 293S cells expressing cloned human κ, δ and μ receptors and neomycin resistance are grown in suspension at 37° C. and 5% CO$_2$ in shaker flasks containing calcium-free DMEM10% FBS, 5% BCS, 0.1% Pluronic F-68, and 600 µg/ml geneticin.

Membrane Preparation

Cells are pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension is spun at 1000 g (max) for 10 min at 4° C. The supernatant is saved on ice and the pellets resuspended and spun as before. The supernatants from both spins are combined and spun at 46,000 g(max) for 30 min. The pellets are resuspended in cold Tris buffer (50 mM Tris/Cl, pH 7.0) and spun again. The final pellets are resuspended in membrane buffer (50 mM Tris, 0.32 M sucrose, pH 7.0). Aliquots (1 ml) in polypropylene tubes are frozen in dry ice/ethanol and stored at −70° C. until use. The protein concentrations are determined by a modified Lowry assay with sodium dodecyl sulfate.

Ligand Binding Assays

The binding affinities of the compounds toward κ, δ or µ receptors are determined by measuring their activities to displace the radioligand binding to the receptors in the membranes using a scintillation proximity assay (SPA) format. The compounds are dissolved in DMSO, 3-fold serial-diluted with DMSO to 11 concentrations and transferred at 2 µl/well onto 96-well white assay plate. The cell membranes with κ, δ or κ receptors are thawed at 37° C., cooled on ice, passed 3 times through a 25-gauge needle, and then mixed with the suspension of wheat germ agglutinin-coated PVT SPA beads (PVT-WGA SPA) in binding buffer (50 mM Tris, 3 mM MgCl$_2$, 1 mg/ml BSA, pH 7.4, which is stored at 4° C. after filtration through a 0.22 m filter). After 30 min on ice, 100 µl of the mixture of membrane and SPA beads are added to each well of the 96-well assay plate containing 2 µl diluted compound.

The radioligands for the binding assay are $^{125}$I Deltorphin II for δ receptor, [$^3$H]-U69593 for κ receptor, and [$^{125}$I]-Enkephalin for µ receptor, respectively. Naloxone is used to define non-specific binding. The binding reaction is initiated by adding 100 µl/well radioligands diluted in Binding Buffer to the assay plate containing compounds, membranes and SPA beads. The final concentrations of the ligands are 40 pM for $^{125}$I Deltorphin II, 0.6 nM for [$^3$H]-U69593 and 0.1 nM for [$^{125}$I]-Enkephalin. The plates containing binding mixtures are left on a shaker for 60 to 120 min at room temperature. After spinning in a centrifuge at 2000 rpm for 5 min, the radioactivity in each well of the paltes is measured by a Topcount Reader (Perkin-Elmer Instrument). Total (TB) and nonspecific (NS) binding are determined in the absence and presence of 10 µM naloxone respectively.

Functional Assays

The agonist activities of the compounds are measured by determining the degrees to which the compounds stimulate the binding of GTP[γ]$^{35}$S to the receptor-G-proteins complex in the membranes. The $EC_{50}$ and $E_{max}$ values of compounds are determined from analysis of the concentration-response curves. The compounds are dissolved in DMSO, 3-fold serial-diluted with DMSO to 11 concentrations and transferred at 2 µl/well onto 96-well white assay plate. The cell membranes with κ, δ or µ receptors are thawed at 37° C., cooled on ice, passed 3 times through a 25-gauge needle, and then mixed with the suspension of wheat germ agglutinin-coated PVT SPA beads (PVT-WGA SPA) in GTPγS assay buffer (50 mM HEPES, 150 mM NaCl, 5 mM $MgCl_2$, 1 mM EGTA, 0.2 mM DTT, 1 mg/ml BSA, pH 7.4). After 30 min on ice, 100 µl of the mixture of membrane and SPA beads are added to each well of the 96-well assay plate containing 2 µl diluted compound.

GTP[γ]$^{35}$S is diluted with GTPγS assay buffer to 0.2 nM, mixed with 20 µM GDP, and 100 µl of the mixture is added each well of the assay plate containing compounds, membranes and SPA beads. After shaking at room temperature for 45 to 60 min, the plates are spin in a centrifuge at 2000 rpm for 5 min, and GTP[γ]$^{35}$S binding activities are determined by measuring the radioactivity in a Topcount Reader (Perkin-Elmer Instrument).

Data Analysis

The specific binding (SB) was calculated as TB-NS, and the SB in the presence of various test compounds was expressed as percentage of control SB. Values of $IC_{50}$ and Hill coefficient ($n_H$) for ligands in displacing specifically bound radioligand are calculated from Excel Fit. Values of $K_i$ were calculated from the Cheng-Prussoff equation. Mean±S.E.M.

Physical Properties and in vitro Drug Metabolism and Pharmacokinetic Properties

It is found that the compound of the invention achieves one or more desirable physical properties and in vitro drug metabolic and pharmacokinetic properties based on the tests using the following assays.

Solubility:

The thermodynamic solubility of the compound(s) in the present invention was determined by stirring a known amount of the compound at 25° C. for 24 hours in a 100 mM phosphate buffer at pH 7.4. An aliqout of the saturated solution was then taken and its concentration measured by liquid chromatography/tandem mass spectrometry (LC/MS/MS). LC/MS/MS experimental conditions and instrumental parameters are described in detail in the LC/MS/MS section.

Log D:

The determination of log D was based on the shake-flask principle. The compound(s) of the present invention was slurried in an octanol-saturated buffer solution and sonicated to promote dissolution. The solution was filtered to remove any insoluble. After an initial sample was taken, the solution volume is adjusted to 10 ml, and a known volume of buffer-saturated octanol is added. The two-phase solution is mixed, then separated by centrifugation. A second sample from the bottom layer (aqueous layer) was then taken. Both samples, which represented the solution concentrations of the compound before and after addition of octanol, were determined by LC/MS/MS. The determined concentrations were used to calculated the log D value.

Metabolic Stability:

The in vitro metabolic stability of the compound(s) in the present invention was determined using human liver microsomes as the enzyme source. The compounds (final concentration, 1 uM) are incubated with human liver microsomes and NADPH. At various times, incubations are sampled and analyzed by LC/MS/MS to determine the loss of parent compound. The intrinsic clearance (CLint) was determined based on the first order elimination rate of the parent compound.

LC/MS/MS Analysis:

All in vivo samples were quantified by LC/MS/MS using a Micromass Quattro Ultima MS/MS system (Waters, Milford, Mass.) fitted with a Shimadzu LC-10 HPLC system (Shimadzu Scientific Systems, Columbia, Md.) and a CTC-Pal autosampler (Leap Technologies, Carrboro, N.C.). The specific LC/MS conditions used are summarized below:

| | |
|---|---|
| MS ionization: | Electrospray |
| Other MS settings: | QuanOptimize was used for automated MS optimization |
| Flow rate: | 1.5 mL/min |
| Column: | Phenomenex Max-RP 30 mm × 2 mm, 4u or equivalent. |
| Column temperature: | Room Temperature |
| Run time: | 2 min. |
| Gradient: | (A) 0.1% formic acid (10 mM ammonium formic and 0.02% |
| | (B) 90% ACN/10% Methanol |

| MS/MS condition Gradient method | | |
|---|---|---|
| Time (min) | A | B |
| 0 | 100 | 0 |
| 0.3 | 100 | 0 |
| 1.3 | 5 | 95 |
| 1.5 | 5 | 95 |
| 1.6 | 100 | 0 |
| 2.0 | 100 | 0 | hERG Assay

The compound may be tested for inhibition of the human ether-a-go-go-related gene (hERG)-encoded K+ channel using a planar-array-based, medium-throughput electrophysiology (IonWorks™ HT). A detailed description of this assay by Bridelan-Taylor et al. has been published in Journal of Pharmacological and Toxicological Methods, 54 (2006), pages 189-199, which is incorporated by reference herein for its disclosure on the IonWorks™ HT. The results of this test is shown in the table below.

Geller-Siefter—Anxiety Model Method

In the conflict test, hungry animals are trained to lever-press for food delivery in a standard operant chamber under two conditions. In the first condition, referred to as the unsuppressed component, food is delivered on average after 17 lever-presses are made (also called a VR17 schedule of reinforcement). In the second condition, referred to as the suppressed component and signalled by flashing lights inside the operant chamber, food is also delivered following an average of 17 lever-presses, but electric shock is additionally delivered to the floor of the cage under a separate VR17 schedule. Daily sessions consist of 5 alternating presentations of each component type: suppressed (3 min in duration) and unsuppressed (2 min in duration). The number of lever presses emitted in the suppressed component is obviously low relative to the unsuppressed component. Anti-anxiety agents, such as diazepam, increase the number of lever-presses that the animals will make in the suppressed component within some range of doses, without altering the number of lever presses that are made in the unsuppressed component. Certain compounds of the invention profile as an anxiolytic in this procedure.

The following table shows some of the biological data of the compound of the invention measured using one or more of the above described assays.

| | |
|---|---|
| Delta Binding CR IC50 | 0.3 nM |
| Delta Agonist GTPgS EC50 | 11 nM |
| Delta Agonist GTPgS % effect max | 114% |
| Mu Binding IC50 | 464 nM |
| Kappa Binding IC50 | 620 nM |
| Solubility | >500 µM |
| logD | 1.6 |
| Human Microsomes CLint @ 1E–06M | 35 µL/min/mg |
| hERG Ion Works IC50 | 18 µM |
| hERG Ion Works % effect max | 62% |

EXAMPLES

The invention will further be described in more detail by the following Examples which describe methods whereby compounds of the present invention may be prepared, purified, analyzed and biologically tested, and which are not to be construed as limiting the invention.

All temperatures are in degrees Celsius (° C.). Unless otherwise stated, operations were carried out at room or ambient temperature (18-25° C.).

Unless otherwise noted, commercial reagents used in preparing the example compound and intermediates were used as received without additional purification.

Unless otherwise noted, the solvents used in preparing the example compound and intermediates were commercial anhydrous grades and used without further drying or purification.

The following abbreviations are employed herein: aq.: aqueous; $CH_2Cl_2$: dichloromethane; DMF dimethylformamide; EtOAc: ethyl acetate; h: hour(s); HPLC: high performance liquid chromatography; HCl: hydrochloric acid; iPrOH: isopropyl alcohol; $K_2CO_3$: potassium carbonate; MeOH: methanol; $NaHCO_3$: sodium bicarbonate; $Na_2SO_4$: sodium sulfate; $NH_3$: ammonia; POPd: dihydrogen dichlorobis(di-tert-butyl phosphinito-kP) palladate(2-); min.: minutes; MS: mass spectrum; NMR: nuclear magnetic resonance; and TBTU: O-(benzotriazol-1-yl)-N,N,N',N'-tetramethyluronium tetrafluoroborate.

Example 1

N-(2-hydroxyethyl)-N-methyl-4-(quinolin-8-yl(1-(thiazol-4-ylmethyl)piperidin-4-ylidene)methyl)benzamide 1A. 4-(Bromo-{4-[(2-hydroxy-ethyl)-methyl-carbamoyl]-phenyl}-methylene)-piperidine-1-carboxylic acid tert-butyl ester N-Methylmorpholine (6.7 mL, 60 6 mmol) and 4-[bromo-(4-carboxy-phenyl)-methylene]-piperidine-1-carboxylic acid tert-butyl ester (prepared as for compound 5 in WO2001074806) (20.0 g, 50.5 mmol) in DMF (240 mL) were treated with TBTU (17.8 g, 55.6 mmol) under nitrogen. After stirring for 10 min., 2-(methylamino)ethanol (5.3 mL, 65.7 mmol) was added and the solution stirred for 2 h. The reaction was diluted with EtOAc (350 mL), washed with 2% citric acid, 3% $NaHCO_3$, and brine. The aq. washes were extracted with EtOAc (50 mL). The combined organic phases were dried over $Na_2SO_4$ then concentrated in vacuo to a solid. After stirring in hexanes for 5 h, the white solid was collected by filtration and dried under high vacuum to afford 21.0 g (92%) of 1A. $^1$H NMR (500.333 MHz, $CDCl_3$) δ 7.44 (d, J=8.0 Hz, 2H), 7.32 (d, J=8.0 Hz, 2H), 3.91 (br s, 2H), 3.74 (br s, 2H), 3.54 (t, J=5.8 Hz, 3H), 3.34 (t, J=5.7 Hz, 2H), 3.09 (s, 3H), 3.01 (br s, 1H), 2.64 (t, J=5.9 Hz, 2H), 2.23 (t, J=5.8 Hz, 2H), 1.47 (s, 9H). MS ES+ 453.1.

1B. 4-({4-[(2-Hydroxy-ethyl)-methyl-carbamoyl]-phenyl}-quinolin-8-yl-methylene)-piperidine-1-carboxylic acid tert-butyl ester Compound 1A (4.0 g, 8.8 mmol), 8-quinolineboronic acid (3.0 g, 17 6 mmol), POPd (0.088 g, 0.18 mmol), and $K_2CO_3$ (3.6 g, 26 4 mmol) in iPrOH (90 mL) were stirred in a preheated 100° C. oil bath under nitrogen for 20 h. The reaction was filtered through celite and concentrated. The material was purified by chromatography on silica gel (gradient 2-5% MeOH in $CH_2Cl_2$) to give a yellow solid 1B (3.27 g, 74%). $^1$H NMR (500.333 MHz, $CDCl_3$) δ 8.91 (dd, J=4.0, 1.6 Hz, 1H), 8.13 (dd, J=8.2, 1.5 Hz, 1H), 7.74 (dt, J=9.5, 3.5 Hz, 1H), 7.50 (d, J=2.5 Hz, 2H), 7.37-7.33 (m, 5H), 3.86 (br s, 2H), 3.68 (br s, 2H), 3.59 (br s, 2H), 3.52-3.43 (m, 3H), 3.34-3.23 (m, 2H), 3.03 (s, 3H), 2.57-2.52 (m, 2H), 2.01 (dd, J=19.3, 7.6 Hz, 2H), 1.44 (s, 9H). MS ES+ 502.2.

1C. N-(2-Hydroxy-ethyl)-N-methyl-4-(piperidin-4-ylidene-quinolin-8-yl-methyl)-benzamide Compound 1B (4.7 g, 9.3 mmol) was treated with 4N HCl in dioxane (30 mL). 10 min. later, the mixture was decanted, and the solid was stirred in ether (40 mL) for 2 h. The ether was then decanted and the remaining yellow solid dried under high vacuum to yield 3.7 g 1C (100%). $^1$H NMR (300.132 MHz, DMSO, 90° C.) δ 8.98 (s, 1H), 8.47 (d, J=8.1 Hz, 1H), 7.96 (d, J=6.6 Hz, 1H), 7.69-7.57 (m, 3H), 7.38 (d, J=8.0 Hz, 2H), 7.29 (d, J=8.3 Hz, 2H), 3.53 (t, J=5.8 Hz, 2H), 3.36 (t, J=5.7 Hz, 2H), 3.23 (t, J=6.0 Hz, 2H), 3.07 (t, J=6.0 Hz, 2H), 2.92 (s, 3H), 2.63 (t, J=6.0 Hz, 2H), 2.15 (t, J=6.0 Hz, 2H). TOF MS ES+ 402.17.

1D. N-(2-hydroxyethyl)-N-methyl-4-(quinolin-8-yl (1-(thiazol-4-ylmethyl)piperidin-4-ylidene)methyl) benzamide Compound 1C (3.3 g, 8.3 mmol) and 4-thiazolecarboxaldehyde (1.4 g, 12.4 mmol) in dichloroethane (16 mL) were stirred for 30 min. under nitrogen. Sodium triacetoxyborohydride (5.3 g, 24 9 mmol) was added and the reaction was stirred for 20 h. The mixture was diluted with $CH_2Cl_2$ (20 mL) and washed with saturated aqueous $NaHCO_3$. The organic phase was dried over $Na_2SO_4$ and concentrated. Column chromatography (120 g silica gel, eluting with 4% 7N $NH_3$/MeOH in $CH_2Cl_2$) gave 2.01 g 1D as a white solid (49%). $^1$H NMR (500.333 MHz, CDCl3) δ 8.90 (dd, J=4.1, 1.7 Hz, 1H), 8.76 (d, J=1.9 Hz, 1H), 8.11 (dd, J=8.0, 1.5 Hz, 1H), 7.72 (dd, J=7.3, 2.3 Hz, 1H), 7.51-7.46 (m, 2H), 7.37-7.33 (m, 3H), 7.31-7.29 (m, 2H), 7.18 (s, 1H), 3.85 (s, br, 2H), 3.76 (s, 2H), 3.67 (br s, 2H), 3.26 (br s, 1H), 3.02 (s, 3H), 2.78-2.71 (m, 1H), 2.67-2.52 (m, 4H), 2.46-2.37 (m, 1H), 2.14-2.04 (m, 2H). TOF MS E+ 499.21.

What is claimed is:

1. A method comprising treating a condition selected from pain, anxiety, depression, Parkinson's disease, and anxious depression in a warm-blooded animal by administering to said animal in need of such treatment a therapeutically effective amount of a compound selected from N-(2-hydroxyethyl)-N-methyl-4-(quinolin-8-yl(1-(thiazol-4-ylmethyl)piperidin-4-ylidene)methyl)benzamide, or pharmaceutically acceptable salt thereof, or mixture thereof.

2. The method according to claim 1, wherein the condition is anxiety.

3. The method according to claim 1, wherein the condition is depression.

4. The method according to claim 1, wherein the condition is Parkinson's disease.

5. The method according to claim 1, wherein the condition is anxious depression.

6. The method according to claim 1, wherein the condition is pain.

7. A method comprising treating a condition selected from pain, anxiety, depression, Parkinson's disease, and anxious depression in a warm-blooded animal by administering to said animal in need of such treatment a pharmaceutical composition comprising a therapeutically effective amount of a compound selected from N-(2-hydroxyethyl)-N-methyl-4-(quinolin-8-yl(1-(thiazol-4-ylmethyl)piperidin-4-ylidene)methyl)benzamide, or pharmaceutically acceptable salt thereof, or mixture thereof and a pharmaceutically acceptable carrier.

8. The method according to claim 7, wherein the condition is anxiety.

9. The method according to claim 7, wherein the condition is depression.

10. The method according to claim 7, wherein the condition is Parkinson's disease.

11. The method according to claim 7, wherein the condition is anxious depression.

12. The method according to claim 7, wherein the condition is pain.

* * * * *